United States Patent [19]

Itatani et al.

[11] Patent Number: 4,581,469

[45] Date of Patent: Apr. 8, 1986

[54] METHOD FOR PRODUCING BIPHENYLTETRACARBOXYLIC ESTERS

[75] Inventors: Hiroshi Itatani; Akinori Shiotani; Mikio Fujimoto, all of Ichihara, Japan

[73] Assignee: UBE Industries, Ltd., Yamaguchi, Japan

[21] Appl. No.: 645,606

[22] Filed: Aug. 29, 1984

[30] Foreign Application Priority Data

Aug. 30, 1983 [JP] Japan .................................. 58-157232

[51] Int. Cl.$^4$ ........................................... C07C 67/343
[52] U.S. Cl. ........................................ 560/96; 560/76
[58] Field of Search .................................... 560/96, 76

[56] References Cited

U.S. PATENT DOCUMENTS

| | | | |
|---|---|---|---|
| 3,857,874 | 12/1974 | Ichikawa et al. | 560/96 X |
| 3,983,159 | 9/1976 | Ichikawa et al. | 560/96 X |
| 4,292,435 | 9/1981 | Itatani et al. | 560/96 |
| 4,338,456 | 7/1982 | Itatani et al. | 560/96 |

Primary Examiner—Natalie Trousof
Assistant Examiner—Vera C. Clarke
Attorney, Agent, or Firm—Burgess, Ryan & Wayne

[57] ABSTRACT

A biphenyltetracarboxylic ester, particularly, 3,3',4,4'-biphenyltetracarboxylic tetraester, is prepared in an increased yield by first oxidative coupling, at 140° C. to 260° C., an o-phthalic diester with a molecular oxygen-containing gas, for example, air, in the presence of a catalyst comprising predetermined amounts of a Pd salt, a basic bidentate ligand compound, and a Cu salt to convert a portion of the o-phthalic diester to the corresponding biphenyltetracarboxylic ester and by additionally oxidative coupling in one or more steps, in each step, the remaining portion of o-phthalic diester with a molecular oxygen-containing gas at 140° C. to 260° C. while controlling the composition of the catalyst to an extent such that the entire molar amount of the Pd salt is 0.0001 to 0.01 time that of the o-phthalic diester, the entire molar amount of the ligand compound is 0.5 to 4 times that of the Pd salt and the entire molar amount of the Cu salt is 0.01 to 5 times that of the Pd salt.

19 Claims, No Drawings

METHOD FOR PRODUCING BIPHENYLTETRACARBOXYLIC ESTERS

BACKGROUND OF THE INVENTION

1. Field of the Invention

The present invention relates to a method for producing biphenyltetracarboxylic esters. More particularly, the present invention relates to an improved method for producing biphenyltetracarboxylic esters from orthophthalic diesters with high selectivity and yield in a two or more-step oxidative coupling procedure in the presence of a catalyst, while the composition of the catalyst is controlled.

2. Description of the Prior Art

In Japanese Unexamined Patent Publication (Kokai) No. 55-153747, the present inventors disclosed a process for producing 3,3',4,4'-biphenyltetracarboxylic tetraesters (s-BPTT) by the selective oxidative coupling reaction of orthophthalic diesters in a molecular oxygen-containing atmosphere in the presence of a catalyst consisting of an organic palladium salt and 1,10-phenanthroline and/or $\alpha,\alpha'$-bipyridyl or a chelate compound of the above-mentioned two compounds at an elevated temperature.

Also, Japanese Unexamined Patent Publication (Kokai) No. 56-46844 discloses a similar process to that disclosed in Japanese Unexamined Patent Publication No. 55-153747, except that the molecular oxygen-containing gas is bubbled into the reaction mixture containing orthophthalic diester and the catalyst.

However, the present inventors found that in the above-mentioned processes, the yield of s-BPTT calculated based on the amount of the orthophthalic diester used is not always satisfactory and the reaction yield of s-BPTT calculated based on the amount of the palladium compound used, which is very expensive, is also not always satisfactory.

U.S. Pat. Nos. 4,292,435 and 4,338,456 disclose a similar process to that disclosed in Japanese Unexamined Patent Publication Nos. 55-153747 and 56-46844, except that the catalyst contains an organic copper salt as a catalytic component in addition to the palladium salt and 1,10-phenanthroline or $\alpha,\alpha'$-bipyridyl. However, these processes are also not always satisfactory in the yield of the resultant biphenyltetracarboxylic ester.

Accordingly, it has been strongly desired to provide a new method which is capable of selectively converting the orthophthalic diesters to the corresponding biphenyltetracarboxylic esters at a high yield based on the amount of the orthophthalic diesters used and the amount of the expensive palladium compound used.

SUMMARY OF THE INVENTION

An object of the present invention is to provide a method for producing biphenyltetracarboxylic esters, particularly, 3,3',4,4'-biphenyltetracarboxylic tetraesters (s-BPTT), by the oxidative coupling reaction of an orthophthalic diester with a high yield based on the amount of the orthophthalic diester.

Another object of the present invention is to provide a method for producing biphenyltetracarboxylic esters, particularly, 3,3',4,4'-biphenyltetracarboxylic tetraesters (s-BPTT), by the oxidative coupling reaction of an orthophthalic diester in the presence of a palladium compound-containing catalyst at a high yield based on the amount of the palladium compound used.

The above-mentioned objects can be attained by the improved method of the present invention, which comprises the steps of: first oxidative coupling, at a temperature of from 140° C. to 260° C., an orthophthalic diester by bringing a molecular oxygen-containing gas into contact with the orthophthalic diester in the presence of a catalyst comprising a palladium catalytic component consisting of at least one palladium salt in a molar amount of 0.00005 to 0.005 times that of the orthophthalic acid, a ligand catalytic component consisting of at least one basic bidentate ligand compound in a molar amount of 0.5 to 4 times that of the palladium component, and a copper catalytic component consisting of at least one copper salt in a molar amount of 0.01 to 5 times that of the palladium component, to convert a portion of the orthophthalic diester used to the corresponding biphenyltetracarboxylic ester; and additionally oxidative coupling, in at least one step, in each step, the remaining portion of the orthophthalic diester by bringing an additional amount of a molecular oxygencontaining gas into contact with the remaining portion of the orthophthalic diester in the presence of the resultant biphenyltetracarboxylic ester produced in the preceding oxidative coupling step and a catalyst at a temperature of from 140° C. to 260° C., while the composition of the catalyst is controlled by adding, in at least one adding operation, at least two members of the palladium, ligand, and copper components to the residual catalyst in the preceding oxidative coupling step, to an extent such that the entire molar amount of the palladium component is within the range of from 0.0001 to 0.01 time that of the orthophthalic diester used, the entire molar amount of the ligand component is in the range of from 0.5 to 4 times that of the palladium component, and the entire molar amount of the copper component is in the range of from 0.001 to 5 times that of the palladium component, to prepare an additional amount of the biphenyltetracarboxylic ester.

DESCRIPTION OF THE PREFERRED EMBODIMENTS

In the method of the present invention, an orthophthalic diester is converted to the corresponding biphenyltetracarboxylic ester, particularly 3,3',4,4'-biphenyltetracarboxylic tetraester (s-BPTT), by means of a catalytic oxidative coupling reaction thereof.

The orthophthalic diester can be prepared by reacting an orthophthalic acid or anhydride or acid halide thereof with an alcoholic compound having a terminal hydroxyl radical, for example, an aliphatic lower alcohol or aromatic alcohol.

The orthophthalic diester usable for the present invention is preferably selected from those of the formula (I):

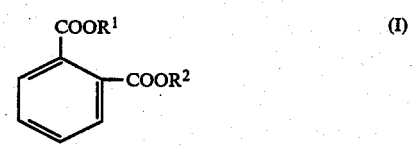

wherein $R^1$ and $R^2$ represent, independently from each other, an alkyl radical having 1 to 5 carbon atoms, respectively.

For example, the orthophthalic diester is selected from the group consisting of dimethyl o-phthalate (DMP), diethyl o-phthalate, dipropyl o-phthalate, dibutyl o-phthalate, and dipentyl o-phthalate.

In the method of the present invention, an oxidative coupling procedure is applied to the orthophthalic diester in the presence of a catalyst consisting of a palladium component, a ligand component, and a copper component.

The palladium catalytic component consists of at least one palladium salt, which may be selected from palladium salts of organic carboxylic acids, palladium chelate salts of β-diketone compounds, and palladium salts of inorganic acids.

The palladium salts of organic carboxylic acids are preferably selected from the group consisting of palladium salts of aliphatic carboxylic acids having 1 to 5 carbon atoms, for example, formic acid, acetic acid, propionic acid, butylic acid, valeric acid, and palladium salts of aromatic carboxylic acid, for example, benzoic acid and terephthalic acid.

The palladium chelate salts of the β-diketone compound are preferably selected from the group consisting of palladium chelate salts, for example, of acetylacetone, benzoylacetone, and trifluoroacetylacetone.

The palladium salts of inorganic acids are preferably selected from the group consisting of palladium salts of hydrochloric acid, nitric acid, nitrous acid, sulfuric acid, sulfurous acid, and phosphoric acid, more preferably, palladium nitrate. Also, the palladium salts usable for the present invention may be in the form of a complex salt. The preferable palladium component for the present invention consists of at least one palladium salt of aliphatic monocarboxylic acids having 1 to 3 carbon atoms, more preferably, palladium acetate.

The basic bidentate ligand compound usable as a catalytic ligand component is preferably selected from the group consisting of 1,10-phenanthroline (Phen) and α,α'-bipyridyl (Bipy). The most preferable ligand compound is 1,10-phenanthroline, because it has an excellent thermal stability.

The copper component for the catalyst of the present invention consists of at least one copper salt. The copper salt is preferably selected from the group consisting of copper salts of organic carboxylic acids, copper chelate salts of β-diketone compounds, and copper salts of inorganic acids.

The copper salts of the organic carboxylic acids are preferably selected from the group consisting of copper salts of aliphatic mono- and di-carboxylic acids having 1 to 5 carbon atoms, for example, formic acid, acetic acid, propionic acid, butylic acid, valeric acid, and oxalic acids.

The copper chelate salts of β-diketone compounds are preferably selected from the group consisting of copper chelate salts of acetylacetone, benzoylacetone, and trifluoroacetylacetone.

The copper salts of inorganic acids usable for the present invention are preferably selected from the group consisting of copper salts of nitric acid, nitrous acid, sulfuric acid, sulfurous acid, and phosphoric acid, more preferably, copper nitrate.

The preferable copper component consists of at least one copper salt of aliphatic monocarboxylic acid having 1 to 3 carbon atoms, more preferable, copper acetate.

The catalyst for each of the first and additional oxidative coupling steps may consist of a mixture of the palladium component, the ligand component, and the copper component or a mixture of a chelating product of the palladium component with the ligand component and the copper component.

The chelating product of the palladium component with the ligand component can be prepared by dissolving the palladium component and the ligand component in an organic solvent, for example, consisting of at least one member selected from benzene, xylene, toluene, acetone, methylene dichloride, and chlorobenzenes, by stirring the resultant solution at room temperature for 0.5 to 10 hours so as to cause the ligand component to be chelated with palladium atom, and by isolating the resultant palladium chelate salt from the reaction mixture.

The molar ratio of the palladium component to the ligand component is preferably in the range of from 1:0.8 to 1:1.5.

In the catalyst for the first oxidative coupling step, the palladium component is in a molar amount of from of 0.00005 to 0.005 times preferably, from 0.0001 to 0.004 times, that of the orthophthalic diester used; the ligand component is in a molar amount of from 0.5 to 4 times, preferably from 0.6 to 3 times, that of the palladium component used; and the copper component is in a molar amount of from 0.01 to 5 times, preferably, from 0.02 to 4 times, that of the palladium component.

If the molar amount of the palladium component is less than 0.00005 times that of the orthophthalic diester, the oxidative coupling reaction of the orthophthalic diester cannot be smoothly carried out. If the molar amount of the palladium component is more than 0.005 times that of orthophthalic diester, the yield of the resultant biphenyltetracarboxylic ester calculated based on the amount of the palladium component undesirably decreases.

If the molar amount of the ligand component is less than 0.5 times that of the palladium component, the degree of selectivity to 3,3',4,4'-biphenyltetracarboxylic tetraester is undesirably poor. Also, if the molar amount of the ligand component is more than 4 times that of the palladium component, the yield of the biphenyltetracarboxylic ester becomes significantly poor. If the molar amount of the copper component is less than 0.01 times that of the palladium component, in the oxidative coupling reaction under about ambient pressure in metallic palladium is undesirably precipitated so as to decrease the yield of the oxidative coupling product. Also, if the molar amount of the copper compound is more than 5 times that of the palladium component, the oxidative coupling reaction rate is reduced so as to cause the yield of the oxidative coupling product to decrease.

In the first oxidative coupling step, a molecular oxygen-containing gas is introduced into a reaction mixture containing the orthophthalic diester, the catalyst, and, optionally, an inert solvent, at a high temperature of from 140° C. to 260° C., preferably, from 160° C. to 250° C. so that a portion of the orthophthalic diester is converted to the corresponding biphenyltetracarboxylic ester.

If the reaction temperature is less than 140° C., the yield of the resultant biphenyltetracarboxylic ester is very poor. Also, a reaction temperature more than 260° C. will cause undesirable side reactions which will produce by-products having a high boiling point and will result in decrease in selectivity to the 3,3',4,4'-biphenyltetracarboxylic tetraester.

In the first oxidative coupling step, it is preferable that the reaction mixture be prepared by mixing predetermined amounts of the palladium, ligand, and copper catalytic components to a predetermined amount of orthophthalic diester at a temperature of from about 5° C. to about 50° C., usually room temperature, and, then, be heated to a desired reaction temperature. Otherwise, it is preferable that predetermined amounts of the palladium, ligand, and copper catalytic components be mixed into a small portion of a predetermined amount of orthophthalic diester and, then, the resultant catalyst be added to the remaining large portion of the orthophthalic diester.

The catalytic components may be mixed into a heated orthophthalic diester at an elevated temperature. If in the first step of this mixing procedure, a palladium component containing a palladium salt of organic or inorganic acid is mixed separately from the other components with the heated orthophthalic diester, sometimes the palladium salt is converted to metallic palladium which deposits from the reaction mixture. Therefore, it is preferable that the palladium component and the ligand component be simultaneously added to the orthophthalic diester or the ligand component first mixed with the orthophthalic diester and, thereafter, the palladium component be added to the orthophthalic diester-ligand component mixture. However, in the case where a chelating compound prepared from a palladium salt and a basic bidentate ligand compound is used, no deposition of metallic palladium occurs.

The first oxidative coupling procedure can be carried out under ambient atmospheric pressure or an increased pressure. In the method of the present invention, it is advantageous in that since the copper salt is used as a catalytic component together with a palladium component, the first oxidative coupling procedure under ambient pressure or a slightly increased pressure never causes the palladium component to be converted to bimetallic palladium (palladium black) which deposits from the reaction mixture, and the activity of the catalyst to be lost. Therefore, the first oxidative coupling procedure is preferably carried out under ambient pressure without using a special high pressure reactor.

In the first oxidative coupling procedure, a molecular oxygen-containing gas is introduced into a reaction mixture containing a predetermined amount of orthophthalic diester and a predetermined amount of a catalyst, so as to dimerize a portion of the orthophthalic diester.

The molecular oxygen-containing gas may be selected from oxygen gas, mixtures of oxygen gas and an inert gas consisting of at least one member selected from, for example, nitrogen, carbon dioxide, neon, and argon gases, and air. In the oxygen gas-inert gas mixture, it is preferable that the content of the oxygen gas be in the range of from 10% to 40% by volume.

In each of the first and additional oxidative coupling steps, it is preferable that the partial pressure of oxygen gas in the reaction system be in the range of from 0.01 to 200 atmospheres, more preferably, from 0.05 to 50 atmospheres.

Also, in the first and additional oxidative coupling steps, the molecular oxygen-containing gas is preferably blown in the form of bubbles into the reaction mixture contained in a reactor. In this bubbling, the molecular oxygen-containing gas is fed from a gas supply source through a bottom plate having a number of perforations, of the reactor, or through a number of nozzles connected to the gas supply source, into the reactor, at a feeding rate of about 10 to 20,000 ml/min, more preferably, 100 to 10,000 ml/min, per 1000 ml of the reaction mixture.

In the process of the present invention, the additional oxidative coupling procedure is carried out in at least one step, preferably, 1 to 10 steps, more preferably, 1 to 6 steps.

In each additional oxidative coupling step of the present invention, the non-reacted portion of orthophthalic diester remaining in the resultant reaction mixture from the preceding step is oxidative-coupled by introducing an additional amount of the molecular oxygen-containing gas into the reaction mixture at a temperature of from 140° C. to 260° C. while the composition of the catalyst in the reaction mixture is controlled by adding, at least two members of the palladium, ligand, and copper components to the residual catalyst in the resultant reaction mixture from the preceding step to an extent such that the entire molar amount of the palladium component is within the range of from 0.0001 to 0.01 time, preferably, from 0.0002 to 0.005 time, that of the orthophthalic diester used, the entire molar amount of the ligand component is in the range of from 0.5 to 4 times, preferably, 0.6 to 3 times, that of the palladium component, and the entire molar amount of the copper component is in the range of from 0.01 to 5 times, preferably, from 0.02 to 4 times, that of the palladium component. In the catalyst composition-controlling procedures, all of the three catalytic components or two members of the three catalytic components, for example, the ligand component with the copper component, the palladium component with the ligand component, or a chelate compound of the ligand component with the palladium component, can be added to the reaction mixture.

In the additional step of the present invention, the remaining portion of the orthophthalic acid in the reaction mixture is converted into the corresponding biphenyltetracarboxylic ester.

In the catalyst composition-controlling procedures in each additional oxidative coupling step, a necessary amount of the afore-mentioned solution of the three catalytic components in a small amount of the orthophthalic diester is added to the reaction mixture or a solution of necessary amounts of two or more members of the three catalytic components in a small portion of the reaction mixture obtained by the completion of the preceding oxidative coupling step, is added into the remaining portion of the reaction mixture.

The additional amounts of the catalytic components are limited to that described above. Preferably, the additional amount of each catalytic components is in the range of from 0.05 to 3 times, more preferably from 0.1 to 2 times, the initial amount of the catalytic component used in the first oxidative coupling step.

In the method of present invention, the reaction time in each oxidative coupling step is variable depending on the reaction conditions (temperature, pressure, type of reactor, etc.) and the amount of the catalyst used. Usually, the reaction time is determined in response to the concentration (amount) of the palladium component. For example, in the case where a palladium component is used in an amount of 0.0001 mole per mole of an orthophthalic diester, the reaction time is preferably in the range of from about 0.2 to 2 hours, more preferably from 0.3 to 1.5 hours. In another example, where a palladium component is used in an amount of 0.6 millimole per mole of an orthophthalic diester, the reaction time is in the range of from about 1.2 to 12 hours, more preferably, from 1.8 to 9 hours. When a catalyst containing the above-mentioned amount of the palladium component is divided into two equivalent portions and the portions are separately added into the reaction mixture, it is preferable that the initial stage reaction time be from about 0.6 to 6 hours and the final stage reaction time be from 0.9 to 4.5 hours.

In the method of the present invention, it is not always necessary to use a reaction medium for orthophthalic diester and the catalyst. However, if necessary, a reaction medium consisting of at least one member selected from organic carboxylic esters, for example, ethyleneglycol diacetate and methyl adipate, and ketone compounds, for example, n-butylmethyl ketone, ethylmethyl ketone, and isopropylethylketone, can be used in a necessary amount.

When a small amount of a "β-diketone compound, for example, acetyl acetone or benzoylacetone or an organic peroxide compound, for example, tert-butyl peroxide, tert-butylhydroxy peroxide, or tert-butyl benzoate, is added to the reaction mixture, the yield of biphenyltetracarboxylic ester sometimes slightly increases.

In the first and additional oxidative coupling steps in accordance with the method of the present invention, an orthophthalic diester used is converted to a main product consisting of a corresponding 3,3',4,4'-biphenyltetracarboxylic tetraester (s-BPTT) at a high reaction yield and a by-product consisting of a corresponding 2,3,3',4'-biphenyltetracarboxylic tetraester (a-BPTT) and substances having high boiling points. Usually, the selectivity to s-BPTT is about 60 molar % or more, sometimes 70 to 95 molar %, based on the entire molar amount of the reaction products.

The resultant s-BPTT can be isolated and collected from the by-product by a known method, for example, distillation and/or deposition.

The collected s-BPTT can be converted to 3,3',4,4'-biphenyltetracarboxylic acid by a known hydrolysis method, for example, a high temperature, high pressure hydrolysis, or an acid or alkali hydrolysis. The resultant 3,3',4,4'-biphenyltetracarboxylic acid may be further converted to 3,3',4,4'-biphenyltetracarboxylic dianhydride. This dianhydride compound is useful as a monomeric material for producing aromatic polyimide resins.

In comparison with the above-mentioned conventional methods, the method of the present invention is highly advantageous not only in that the reaction yield of the resultant biphenyltetracarboxylic ester calculated based on the amount of the orthophthalic diester used or the entire amount of the palladium component in the catalyst used is remarkably high, but also in that the selectivity to s-BPTT is high, that is, the amount of the by-product is small. Therefore, the method of the present invention is industrially superior to conventional methods.

Also, the method of the present invention can be easily utilized for industrial purposes, because the oxidative coupling procedures of the method of the present invention can be carried out not only under an ambient pressure or a slightly increased pressure without using a high pressure reactor, but also by using a simple reaction system consisting of only a reaction mixture containing orthophthalic diester and a catalyst and a molecular oxygen-containing gas.

The specific examples presented below will serve to more fully explain how the present invention is practiced. However, it will be understood that these examples are only illustrative and in no way limit the scope of the present invention.

In the examples, the composition of reaction mixture was determined by means of gas chromatography. From the result of the gas chromatographic analysis, the amounts of 2,3,3',4'-biphenyltetracarboxylic tetraester (a-BPTT) and 3,3',4,4'-biphenyltetracarboxylic tetraester (s-BPTT) and by-products (pitch-like substance having a high boiling point) were calculated.

A percent of conversion of an orthophthalic diester, a percent of yield of a product, and a percent of selectivity to a product were calculated in accordance with the following equation.

Percent of conversion of o-phthalic diester used =

$$\frac{\text{Amount (mole) of o-phthalic diester converted}}{\text{Amount (mole) of o-phthalic diester used}} \times 100$$

Percent of yield of s-BPTT based on the amount of o-phthalic diester used (o-phthalic diester-based yield) =

$$\frac{\text{Amount (mole) of s-BPTT obtained}}{\text{Amount (mole) of o-phthalic diester used} \times 0.5} \times 100$$

Percent of yield of s-BPTT based on the amount of palladium catalytic component used (Pd-based yield) =

$$\frac{\text{Amount (mole) of s-BPTT obtained}}{\text{Amount (mole) of palladium catalytic component used}} \times 100$$

Percent of selectivity to s-BPTT =

$$\frac{\text{Amount (mole) of s-BPTT obtained}}{\text{Entire amount (mole) of o-phthalic diester used} \times 0.5} \times 100$$

EXAMPLE 1

A round bottom flask having a capacity of 300 ml and equipped with a reflux condenser, a thermometer, a stirrer, and an inlet for introducing a gas thereinto was charged with a first reaction mixture which was prepared by mixing 100 ml (119 g) of orthophthalic dimethylester (DMP) with 0.2 m mole (45 mg) of palladium acetate, 0.2 m mole (40 mg) of 1,10-phenanthroline monohydrate, and 0.06 m mole (12 mg) of copper acetate monohydrate at room temperature (about 25° C.).

The reaction mixture was heated to a temperature of 220° C. by using an oil bath. Air was introduced in the form of bubbles into the heated reaction mixture at a flow rate of 300 ml/min for 2 hours to oxidatively couple a portion of the orthophthalic dimethylester.

After the above-mentioned first oxidative coupling procedures were completed, a small 5 ml portion of the resultant reaction mixture was withdrawn from the resultant reaction mixture and mixed with 0.2 m mole of palladium acetate, 0.2 m mole of 1,10-phenanthroline monohydrate, and 0.06 m mole of copper acetate monohydrate at room temperature. The resultant mixture was mixed with the remaining portion of the resultant reaction mixture at a temperature of 220° C.

The resultant second oxidative coupling reaction mixture was subjected to the same procedures as that of the first oxidative coupling reaction for 2 hours. The total reaction time was 4 hours. After the reaction procedures were completed, the same catalytic component-addition procedures as those described above were carried out and the resultant reaction mixture was subjected to the same oxidative coupling reaction as that described above for 2 hours. The total reaction time was 6 hours.

The same catalytic component-addition procedures and oxidative coupling procedures as those mentioned above were further carried out. The resultant reaction mixture was subjected to a further reaction for 4 hours. The total reaction time was 10 hours.

After all of the above-mentioned procedures were completed, the resultant reaction product was subjected to the measurements of percent of conversion of o-phthalic dimethylester, percent of DMP-based yield of s-BPTT, percent of Pd-based yield of s-BPTT, and percent of selectivity to s-BPTT. The results are shown in Table 1.

COMPARATIVE EXAMPLE 1

The same procedures as those described in Example 1 were carried out, except that the flask was charged with a reaction mixture consisting of 100 ml (119 g) of orthophthalic dimetylester, 0.8 m mole (180 mg) of palladium acetate, 0.8 m mole (159 mg) of 1,10-phenanthroline monohydrate, and 0.24 m mole (48 mg) of copper acetate monohydrate and that the oxidative coupling reaction was carried out in a single step for 10 hours under the same conditions as those described in Example 1.

The results are shown in Table 1.

EXAMPLES 2 TO 5 AND COMPARATIVE EXAMPLES 2 AND 3

In each of Examples 2 to 5 and Comparative Examples 2 and 3, the same procedures as those described in Example 1 were carried out, except that the amounts of the catalytic components, the catalytic component-addition stages, the reaction temperature and the reaction times were changed as indicated in Table 1.

The results are shown in Table 1.

TABLE 1

| | | | Oxidative coupling reaction | | | | | | | Oxidative coupling products | | | | | | | | |
|---|---|---|---|---|---|---|---|---|---|---|---|---|---|---|---|---|---|---|
| | Catalytic component addition No. | Total reaction time (hr) | Amount of added catalytic components (m moles) | | | Amount of ortho-phthalic diester (ml) (g) | Flow rate of air (ml/min) | Reaction temperature (°C.) | Conversion of o-phthalic diester (mol %) | s-BPTT | | | | a-BPTT | | High boiling point substance | |
| Example No. | | | Pd component | Ligand component | Cu component | | | | | Amount (g) | DMP-based yield (mol %) | Pd-based yield (mol %) | Selectivity (mol %) | Amount (g) | DMP-based yield (mol %) | Amount (g) | DMP-based yield (mol %) |
| Example 1 | 1 | 0 | 0.2 | 0.2 | 0.06 | | | | | | | | | | | | |
| | 2 | 2 | " | " | " | | | | | | | | | | | | |
| | 3 | 4 | " | " | " | | | | | | | | | | | | |
| | 4 | 6 | " | " | " | | | | | | | | | | | | |
| | — | 10 | | | | 100 (119) | 300 | 220 | 28.03 | 25.43 | 21.37 | 8230 | 76.2 | 1.98 | 1.66 | 5.95 | 5.00 |
| Comparative Example 1 | 1 | 10 | 0.8 | 0.8 | 0.24 | 100 (119) | " | " | 18.52 | 16.38 | 13.76 | 5300 | 74.3 | 1.32 | 1.11 | 4.34 | 3.65 |
| Example 2 | 1 | 0 | 0.4 | 0.4 | 0.12 | | | | | | | | | | | | |
| | 2 | 2 | — | 0.08 | 0.08 | | | | | | | | | | | | |
| | — | 8 | | | | " | " | " | 16.98 | 16.85 | 14.16 | 10910 | 83.4 | 1.34 | 1.13 | 2.02 | 1.69 |
| Comparative Example 2 | 1 | 0 | 0.4 | 0.4 | 0.06 | | | | | | | | | | | | |
| | — | 8 | | | | 100 (119) | 300 | 220 | 12.77 | 12.39 | 10.41 | 8020 | 81.5 | 0.99 | 0.83 | 1.82 | 1.53 |
| Example 3 | 1 | 0 | 0.2 | 0.2 | 0.06 | | | | | | | | | | | | |
| | 2 | 2 | " | " | " | | | | | | | | | | | | |
| | 3 | 4 | " | " | " | | | | | | | | | | | | |
| | 4 | 6 | " | " | " | | | | | | | | | | | | |
| | 5 | 8 | " | " | " | | | | | | | | | | | | |
| | — | 12 | | | | " | " | " | 31.79 | 27.84 | 23.40 | 7210 | 73.6 | 2.08 | 1.75 | 7.90 | 6.64 |
| Example 4 | 1 | 0 | 0.2 | 0.2 | 0.06 | | | | | | | | | | | | |
| | 2 | 2 | " | " | " | | | | | | | | | | | | |
| | 3 | 4 | " | " | " | | | | | | | | | | | | |
| | — | 8 | | | | 100 (119) | 300 | 220 | 23.11 | 22.01 | 18.50 | 9500 | 80.0 | 1.70 | 1.43 | 3.78 | 3.18 |
| Comparative Example 3 | 1 | 8 | 0.6 | 0.6 | 0.18 | " | " | " | 15.77 | 14.54 | 12.22 | 6280 | 77.5 | 1.19 | 1.00 | 3.03 | 2.55 |
| Example 5 | 1 | 0 | 0.2 | 0.2 | 0.06 | | | | | | | | | | | | |
| | 2 | 2 | " | " | " | | | | | | | | | | | | |
| | 3 | 4 | " | " | " | | | | | | | | | | | | |
| | 4 | 6 | " | " | " | | | | | | | | | | | | |
| | — | 10 | | | | | | 210 | 23.32 | 20.61 | 17.32 | 6670 | 74.3 | 1.68 | 1.41 | 5.46 | 4.59 |

EXAMPLE 6

The same first oxidative coupling procedures as those described in Example 1 were carried out, except that the first reaction time was 4 hours. The resultant reaction mixture in the flask was allowed to cool to ambient temperature and then was mixed with 0.2 m mole of palladium acetate, 0.2 m mole of 1,10-phenanthroline monohydrate, and 0.06 m mole of copper acetate monohydrate at ambient temperature. The resultant second reaction mixture was heated to a temperature of 220° C. by using an oil bath for 4 hours while air was blown in the form of bubbles into the second reaction mixture at a flow rate of 300 ml/min. The total reaction time was 8 hours.

The results are shown in Table 2.

EXAMPLE 7

The same first oxidative coupling procedures as those described in Example 6 were carried out, except that the amount of palladium acetate was 0.4 m mole (90 mg), the 1,10-phenanthroline monohydrate was replaced by 0.4 m mole (62 mg) of α,α'-bipyridyl, the amount of the copper acetate monohydrate was 0.4 m mole (80 mg), and the reaction temperature was 200° C.

The resultant reaction mixture from the first oxidative coupling procedures was subjected directly to the next procedure without cooling it. The same catalyst component-addition procedures as those described in Example 1 were applied to the first oxidative coupling reaction mixture, except that the additional amount of palladium acetate was 0.4 m mole, the additional amount of the 1,10-phenanthroline monohydrate was replaced by 0.4 m mole of α,α'-bipyridyl, and the additional amount of the copper acetate monohydrate was 0.4 m mole. Next, a second oxidative coupling procedure was applied to the resultant second oxidative coupling reaction mixture in the same manner as that in the first oxidative coupling step.

The results are shown in Table 2.

COMPARATIVE EXAMPLE 4

The same first oxidative coupling procedures as those described in Example 7 were carried out except that the amounts of the palladium acetate, the α,α'-bipyridyl, and the copper acetate monohydrate were respectively 0.8 m mole (180 mg), 0.8 m mole (124 mg), and 0.8 m mole (160 mg), and the reaction time was 8 hours.

No second oxidative coupling procedures were carried out.

The results are shown in Table 2.

EXAMPLE 8

A solution of 2.128 g (20 m moles) of palladium black in 10 ml of concentrated nitric acid was diluted with 80 ml of water. The diluted palladium black was mixed with a liquid mixture of 3.964 g (20 m moles) of 1,10-phenanthroline monohydrate (20 m moles) with 40 ml of ethyl alcohol by adding dropwise the liquid solution to the diluted palladium black solution. Yellow deposits were produced in the reaction mixture.

The yellow deposits were collected by means of filtration and dried. A chelate product consisting of 1,10-phenanthroline dinitropalladium was obtained in an amount of 7.97 g in a yield of 97%.

The results of elemental analysis of the palladium chelate product were as follows.

|  | C | H | N |
|---|---|---|---|
| Measured | 35.78 | 1.97 | 14.04 |
| Theoretical | 35.10 | 1.96 | 13.65 |

The same procedures as those described in Example 1 were carried out, except that in place of the combination of 0.2 m mole (45 mg) of palladium acetate and 0.2 m mole (40 mg) of 1,10-phenanthroline monohydrate used in Example 1, 0.2 m mole (82 mg) of the above-mentioned palladium chelate compound was used throughout all the stages of the first and second oxidative coupling steps.

The results are shown in Table 2.

COMPARATIVE EXAMPLE 5

The same procedures as those described in Comparative Example 1 were carried out, except that the combination of 0.8 m mole (180 mg) of palladium acetate and 0.8 m mole (159 mg) of 1,10-phenanthroline monohydrate was replaced by 0.8 m mole (328 g) of the same palladium chelate product as that described in Example 8.

The results are shown in Table 2.

TABLE 2

| | Conversion of o-phthalic diester (mol. %) | Oxidative coupling product | | | | | | | |
|---|---|---|---|---|---|---|---|---|---|
| | | s-BPTT | | | | a-BPTT | | High boiling point substance | |
| Example No. | | Amount (g) | DMP-based yield (mol. %) | Pd-based yield (mol. %) | Selectivity (mol. %) | Amount (g) | DMP-based yield (mol. %) | Amount (g) | DMP-based yield (mol. %) |
| Example 6 | 16.76 | 15.59 | 13.10 | 10100 | 78.2 | 1.26 | 1.06 | 3.09 | 2.60 |
| Example 7 | 13.48 | 11.80 | 9.92 | 3820 | 73.6 | 1.70 | 1.43 | 2.53 | 2.13 |
| Comparative Example 4 | 10.71 | 8.77 | 7.37 | 2840 | 68.8 | 1.89 | 1.59 | 2.08 | 1.75 |
| Example 8 | 23.16 | 20.37 | 17.12 | 6596 | 73.9 | 1.96 | 1.65 | 5.22 | 4.39 |
| Comparative Example 5 | 20.61 | 18.29 | 15.37 | 5920 | 74.5 | 1.64 | 1.38 | 4.59 | 3.86 |

We claim:

1. An improved method for producing biphenyltetracarboxylic esters, comprising the steps of:
    first oxidative coupling, at a temperature of from 140° to 260° C., an orthophthalic diester by bringing a molecular oxygen-containing gas into contact with said orthophthalic diester in the presence of a catalyst comprising a palladium catalytic component consisting of at least one palladium salt in a molar amount of 0.00005 to 0.005 times that of said orthophthalic acid, a ligand catalytic component consisting of at least one basic bidentate ligand compound selected from the group consisting of 1,10 phenanthroline and α, α'-bipyridyl in a molar amount of 0.5 to 4 times that of said palladium component, and a copper catalytic component consisting of at least one copoper salt in a molar amount of 0.01 to 5 times that of said palladium component, to convert a portion of said orthophthalic diester to the corresponding biphenyltetracarboxylic ester; and additionally oxidative coupling, in at least one step, in each step, the remaining portion of said orthophthalic diester by bringing an additional amount of a molecular oxygen-containing gas into contact with said remaining portion of said orthophthalic diester in the presence of the resultant biphenyltetracarboxylic ester produced in the preceding oxidative coupling step and a catalyst, at a temperature of from 140° C. to 260° C., while the composition of said catalyst is controlled by adding at least two members of said palladium, ligand, and copper components into the residual catalyst in the preceding oxidative coupling step, to an extent such that the entire molar amount of said palladium component is within the range of from 0.0001 to 0.01 times that of said orthophthalic diester used, the enitre molar amount of said ligand component is in the range of from 0.5 to 4 times that of said palladium component, and the entire molar amount of said copper component is in the range of from 0.01 to 5 times that of said palladium component, to prepare an additional amount of said biphenyltetracarboxylic ester.

2. The method as claimed in claim 1, wherein said orthophthalic diester is a compound of the formula (I):

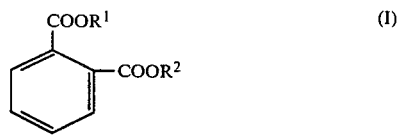 (I)

wherein $R^1$ and $R^2$ represent, independently from each other, an alkyl radical having 1 to 5 carbon atoms.

3. The method as claimed in claim 1, wherein said palladium salt is selected from the group consisting of palladium salts of organic carboxylic acids, palladium salts of inorganic acids, and palladium chelate salts of β-diketone compounds.

4. The method as claimed in claim 3, wherein said palladium salts of organic carboxylic acids are palladium salts of aliphatic mono and di-carboxylic acids having 1 to 5 carbon atoms.

5. The method as claimed in claim 3, wherein said palladium chelate salts of β-diketone compounds are palladium chelate salts of acetylacetone, benzoylacetone, and trifluoroacetylacetone.

6. The method as claimed in claim 3, wherein said palladium salts of inorganic salts are palladium salts of hydrochloric acid, nitric acid, nitrous acid, sulfuric acid, sulfurous acid, and phosphoric acid.

7. The method as claimed in claim 1, wherein said copper salt is selected from the group consisting of copper salts of organic carboxylic acids, copper chelate salts of β-diketone compounds, and copper salts of inorganic acids.

8. The method as claimed in claim 7, wherein said copper salts of organic carboxylic acids are copper salts of aliphatic mono- and di-carboxylic acids having 1 to 5 carbon atoms.

9. The method as claimed in claim 7, wherein said copper chelate salts of β-diketone compounds are copper chelate salts of acetylacetone, benzoylacetone, and trifluoroacetylacetone.

10. The method as claimed in claim 7, wherein said copper salts of inorganic acids are copper salts of nitric acid, nitrous acid, sulfuric acid, sulfurous acid, and phosphoric acid.

11. The method as claimed in claim 1, wherein said palladium component is used in a molar ratio to the ligand component of from 1:0.8 to 1:1.5.

12. The method as claimed in claim 1, wherein each of the first and additional oxidative coupling steps is carried out at a temperature of from 160° C. to 250° C.

13. The method as claimed in claim 1, wherein each of the first and additional oxidative coupling step is carried out each under ambient atmospheric pressure or an increased pressure.

14. The method as claimed in claim 1, wherein said molecular oxygen-containing gas is selected from oxygen gas, mixture gases of oxygen gas with an inert gas consisting of at least one member selected from the group consisting of nitrogen, carbon dioxide, neon, and argon gases, and air.

15. The method as claimed in claim 1, wherein the partial pressure of oxygen gas in the reaction system in each of the first and additional oxidative coupling steps is the range of from 0.01 to 200 atmospheres.

16. The method as claimed in claim 1, wherein in each of the first and additional oxidative coupling step, said molecular oxygen-containing gas is fed in the form of bubbles at a feeding rate of from 10 to 20,000 ml/min per 1000 ml of the reaction mixture.

17. The method as claimed in claim 1, wherein each of said first and additional oxidative coupling step is carried out in a reaction medium.

18. The method as claimed in claim 1, wherein said additional oxidative coupling procedure is carried out in one to 10 steps.

19. The method as claimed in claim 18, wherein said additional oxidative coupling procedure is carried out in one to six steps.

* * * * *